(12) United States Patent
Persson

(10) Patent No.: US 7,017,744 B2
(45) Date of Patent: Mar. 28, 2006

(54) PACKAGE FOR HYGIENIC STORAGE OF ABSORBENT ARTICLES

(75) Inventor: Håkan Persson, Billdal (SE)

(73) Assignee: SCA Hygiene Probucts AB, Göteborg (SE)

( * ) Notice: Subject to any disclaimer, the term of this patent is extended or adjusted under 35 U.S.C. 154(b) by 11 days.

(21) Appl. No.: 10/146,929

(22) Filed: May 17, 2002

(65) Prior Publication Data

US 2002/0170841 A1    Nov. 21, 2002

Related U.S. Application Data

(60) Provisional application No. 60/291,625, filed on May 18, 2001.

(51) Int. Cl.
*A61B 19/02* (2006.01)

(52) U.S. Cl. .................................................. 206/440

(58) Field of Classification Search ................. D3/203, D3/205; 206/440, 449, 494, 497, 581, 823; 220/315, 837–839; 53/399
See application file for complete search history.

(56) References Cited

U.S. PATENT DOCUMENTS

| | | | | |
|---|---|---|---|---|
| 1,268,064 A | * | 5/1918 | Johnson | 220/686 |
| 1,436,406 A | * | 11/1922 | Schulz | 220/319 |
| 1,692,504 A | * | 11/1928 | Hayden | 206/570 |
| 2,478,412 A | * | 8/1949 | McMahan | 206/581 |
| 2,750,033 A | * | 6/1956 | Pickens | 206/361 |
| 3,733,002 A | * | 5/1973 | Fujio | 215/12.2 |
| 4,184,309 A | * | 1/1980 | Amberg | 53/399 |
| 4,458,468 A | * | 7/1984 | Sivilich | 53/428 |
| 4,832,198 A | * | 5/1989 | Alikhan | 206/438 |
| 4,964,526 A | * | 10/1990 | Stephens | 220/520 |
| D359,163 S | * | 6/1995 | Summerfield et al. | D3/205 |
| 5,443,161 A | | 8/1995 | Jonese | |
| 5,564,562 A | | 10/1996 | Focke et al. | |
| 5,579,916 A | * | 12/1996 | Manko | 206/581 |
| 5,722,774 A | | 3/1998 | Hartz | |
| 5,860,550 A | * | 1/1999 | Miller et al. | 220/4.23 |
| D427,764 S | * | 7/2000 | Conway | D3/203 |
| D436,434 S | * | 1/2001 | Conway | D3/203 |

* cited by examiner

*Primary Examiner*—Mickey Yu
*Assistant Examiner*—Jerrold Johnson
(74) *Attorney, Agent, or Firm*—Buchanan Ingersoll PC

(57) ABSTRACT

The present invention concerns a package for hygienic storage of two or more similar, non-folded, thin absorbent articles, preferably micro panty shields, which are placed on top of each other in a stack. The package is shape stable and shockproof and has a container part and a lid part. The container part and the lid part together delimit a storage space intended to accommodate the stack, where the storage space has a form that principally conforms to the form of the stack.

18 Claims, 4 Drawing Sheets

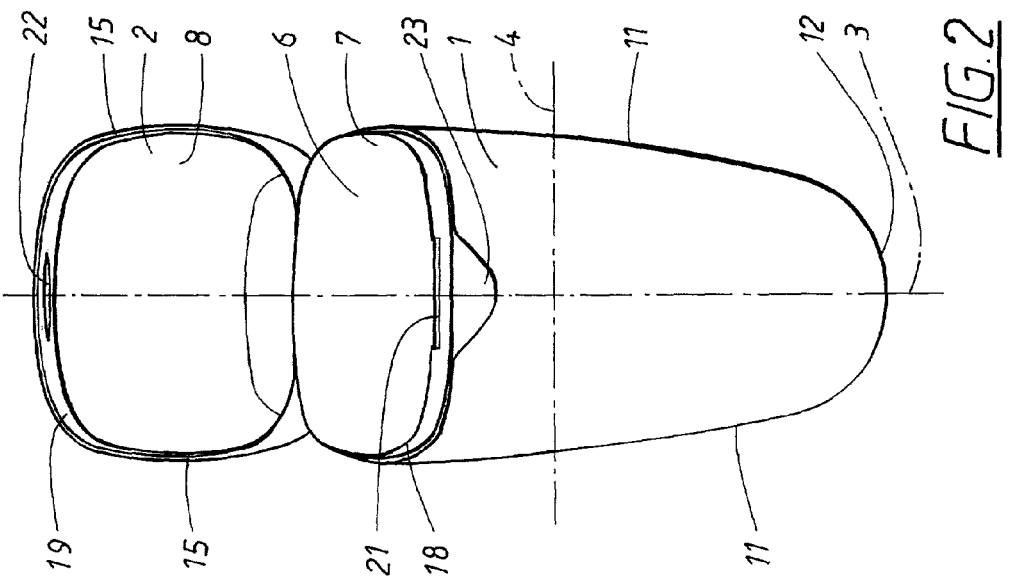
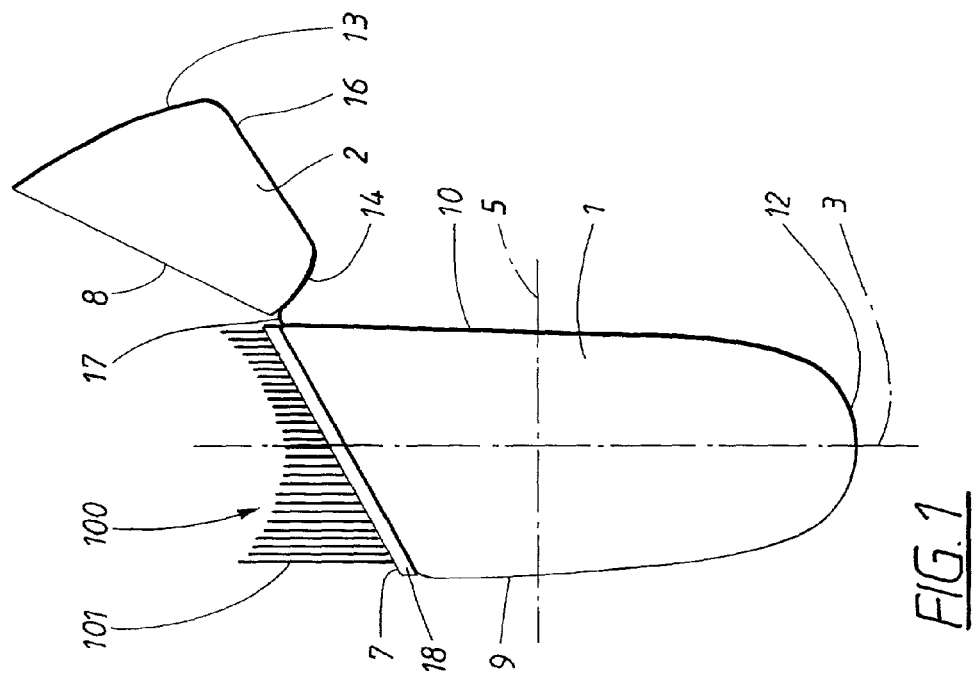

PACKAGE FOR HYGIENIC STORAGE OF ABSORBENT ARTICLES

This application claims priority under 35 U.S.C. §119 to U.S. Provisional Application No. 60/291,625 entitled PACKAGE FOR HYGIENIC STORAGE OF ABSORBENT ARTICLES and filed on May 18, 2001, the entire content of which is hereby incorporated by reference.

FIELD OF THE INVENTION

The present invention concerns a package for hygienic storage of two or more similar, non-folded, thin absorbent articles, which are placed on top of each other in a stack, such as panty shields, thin sanitary napkins or similar small personal hygiene products, preferably so-called micro panty shields. The package is shape stable and shockproof and comprises a container part and a lid part.

BACKGROUND INFORMATION

Conventional packages for absorbent articles of this type are usually manufactured from cardboard or plastic and often contain a number of articles packed beside one another. The individual articles can either be packed in the package as they are or in so-called single-wrap packages, where each article is usually wrapped in a plastic film. With a single-wrap package, the article itself does not come into contact with the environment until it is time to use the article, which is advantageous from a hygienic aspect. A commonly occurring type of package is cardboard boxes which are parallelepipedic, cubic or have some other polyhedral form and contain a number of articles, which can be singly wrapped. Another variation is that a number of articles, which are normally singly wrapped, are packed in bags of plastic, such as polyethylene.

A problem with this type of packages is that, in order to obtain hygienic storage of the absorbent articles, they must be singly wrapped. Single wrapping in itself is complicated from the point of view of both manufacturing and process engineering and it is also expensive as each individual sanitary napkin or panty shield must be wrapped in plastic.

The articles are also often folded in connection with the single wrapping to make them smaller in size. The folding in itself complicates the manufacturing and can have a negative effect on the liquid absorption ability of the articles as well as often giving the articles a less attractive appearance. If the articles are not singly wrapped but are placed as they are in a box or in a plastic bag, there is a risk that dirt, dust or the like will end up on the articles, which can lead to the articles not being perceived as fresh during use. Another problem with conventional packages is that they are not suited to being taken in a handbag or the like. The box or the plastic bag that they are made of easily breaks or is compressed, which can lead to the individual articles falling out of the package. One solution to the problem can be that the user takes along individual singly-wrapped articles, with the risk of the single-wrap packages splitting or not protecting the article sufficiently.

Examples of packages for a plurality of absorbent articles are given in WO 96/24537 A1 and WO 98/06369 A1, and examples of singly wrapped absorbent articles are given in WO 88/10219 A1, WO 91/18574 A1 and EP 0 675 703 B1.

In U.S. Pat. No. 4,964,526, a package for hygiene products, such as sanitary napkins, panty shields or tampons is described. The package is designed so that a number of hygiene products can easily be carried by a user. The disadvantage with a package of this type is that it is not adapted for a specific type of absorbent article but is so spacious that a number of different types and sizes of hygiene products can be stored in it. As the package is not optimized for a certain type of absorbent article, it is not suitable for compact storage, transport and retail.

Similar packages or containers which are adapted for a specific type of absorbent article are also described in GB 2 269 162 A, U.S. Pat. Nos. 5,579,916 A and U.S. Pat. No. 3,557,853 A.

SUMMARY OF THE INVENTION

The aim of the present invention is to remedy the above problem and to construct a hygienic package which effectively protects the absorbent articles from dirt, dust or the like without the need for them to be singly wrapped.

The package for hygienic storage of two or more similar absorbent articles which are placed on top of each other in a stack, such as panty shields, thin sanitary napkins or similar small hygiene products, preferably so-called micro panty shields, in accordance with the present invention is distinguished in that it is shape stable and shock-proof and comprises a container part and a lid part, wherein the container part and the lid part together delimit a space intended to accommodate said stack and that the space has a form that principally conforms to the form of the stack.

DESCRIPTION OF THE INVENTION

Through the present invention, a package of the type mentioned in the description has been achieved, which package essentially eradicates the problems mentioned above with respect to the prior art.

The package includes a container part and a lid part. The container and lid parts are intended to together enclose a number of adjacent, non-folded absorbent articles, preferably micro panty shields, placed on top of one another in a stack. The package has a three-dimensional form with a longitudinal direction, a transverse direction and a height direction, where the different directions are perpendicular or essentially perpendicular to one another. The package is provided with a storage space which has a form which essentially corresponds to the form that the stack of panty shields has when packaged.

The container part suitably has an elongate form with a front surface, a rear surface opposite to the front surface, two side surfaces opposite to each other and an end surface. In the same way as the container part, the lid part has a front surface, a rear surface opposite to the front surface, two side surfaces opposite to each other and an end surface. The end surface on the lid part is preferably flat so that during transport and sale the package can stand upright with the lid part arranged downwards and the container part upwards.

The container part is provided with an opening which is adapted to an opening arranged on the lid part in such a way that a tight seal is obtained between the container and lid parts in order to avoid dirt, dust or the like penetrating into the package. The two openings are situated at a distance from and opposite to the end surface of each respective part. The opening of the container part thus has a periphery that is delimited by the forward, rear and side surfaces of the container part. In the same way, the opening of the lid part has a periphery that is delimited by the forward, rear and side surfaces of the lid part.

The package is opened by the lid part being removed from or displaced in relation to the container part. In accordance with one preferred embodiment, the lid part is joined to the container part by means of a joint member, such as a hinge, which is placed so that the rear surface of the container part is connected to the rear surface of the lid part. In this way, the lid part is pivotably joined in relation to the container part.

In order to prevent dirt, dust or the like from penetrating into the package, a rim is arranged on the container part, suitably along the entire periphery on the opening of the container part. In a corresponding manner, the area along the periphery on the opening of the lid part is suitably provided with a recess. The rim is adapted to the recess and in a closed position the rim ends up in the recess, with the result that the rim and the recess together give a tight seal.

An important property for the package is that it is shockproof and is formed so that the lid part sits securely on the container part so that the package does not open of its own accord when it is being stored or is subjected to blows or knocks. As the package is suitably provided with a locking mechanism in the form of a snap lock, it is possible to ensure safe storage of the panty shields. The snap lock is suitably arranged in connection with the rim and the recess. By giving the package a form that is adapted to its purpose and by manufacturing it from suitable material, it can also be made shape stable. The expression shape stable is intended to mean that the package is not deformed to any appreciable degree under the loads it can be subjected to during normal use. The fact that the package is shape stable also means that it shall be able to revert to its original form after having been subjected to the deformation.

Suitable materials for the package are plastics, such as polystyrene (PS), polyvinyl chloride (PVC), polyethylene (PE), polypropylene (PP) and polyethylene terephthalate (PET). By using a transparent or semi-transparent material during manufacture, the package can be formed so that it is possible to see the stack of panty shields from its outside. It is also possible to make a part of the package transparent or semi-transparent, for example by arranging a window on the package through which it is possible to see the absorbent articles. Another alternative can be that only the lid part or the container part is made transparent or semi-transparent. The package is advantageously manufactured by means of injection moulding, blow moulding or vacuum forming.

BRIEF DESCRIPTION OF THE DRAWINGS

The invention will be described below in more detail with reference to the embodiments shown in the figures.

FIG. 1 shows an open package in accordance with the invention seen from the side.

FIG. 2 shows the open package seen from the front.

DETAILED DESCRIPTION OF THE PREFERRED EMBODIMENTS

Figure 4:
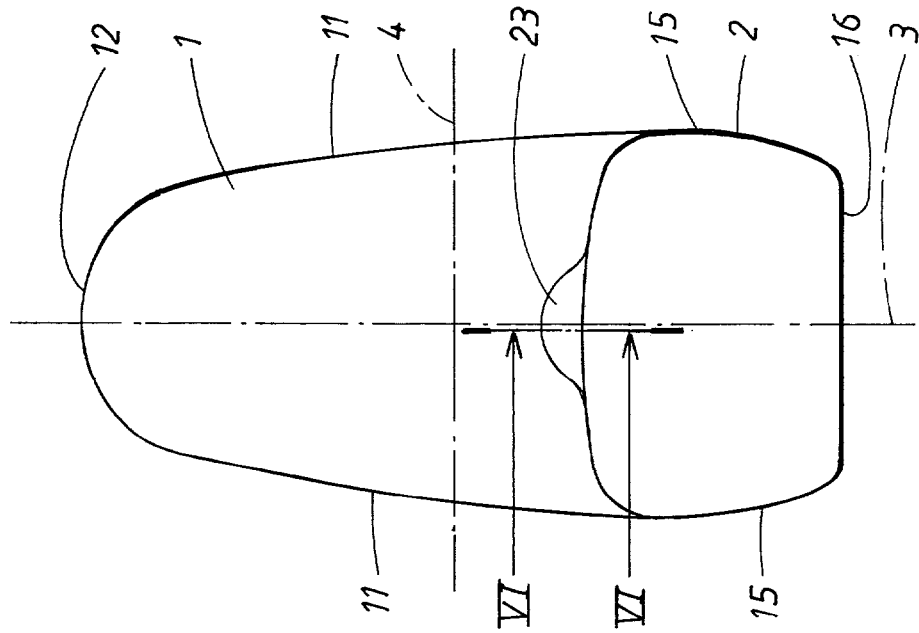
FIG. 4 shows the closed package seen from the front.

A package for storing absorbent articles is shown in FIGS. 1–5. The package includes a container part 1 and a lid part 2. The container and lid parts are intended to together enclose a number of non-folded micro panty shields, or similar absorbent articles 101 which are placed against each other in a stack 100 on top of each other. A micro panty shield is distinguished by the fact that it has a small extension in the longitudinal and transverse directions compared with a traditional panty shield. The package has a three-dimensional form with a longitudinal direction 3, a transverse direction 4 and a height direction 5, where the different directions are perpendicular or essentially perpendicular to each other. The package has a storage area 6 which is delimited by the container part 1 and the lid part 2. The storage area 6 has a form, i.e. an extension in the longitudinal, transverse and height directions which essentially corresponds to the extension which the stack 100 of panty shields has during packaging. Due to the fact that the form of the package is adapted to the stack, it can be made compact, small, neat and easy for a user to carry around. It is expedient for the storage area 6 to have a somewhat greater extension in the longitudinal, transverse and height directions than the stack 100 to make it easy to place the panty shields in the package during the actual packaging stage in the manufacturing process. Due to the form of the storage area 6, the package encloses the stack 100 in such a way that the panty shields lie securely during transport and storage.

The container part 1 is provided with an opening 7 which cooperates with an opening 8 on the lid part 2 in such a way that a tight seal is obtained between the container and lid parts 1, 2 in order to avoid dirt, dust or the like penetrating into the package.

The container part 1 can have any form that is suitable for the articles to be stored in it as long as it is adapted to cooperate with the lid part 2 by means of the container part together with the lid part forming a space which essentially corresponds with the extension defined by the stack of panty shields. In FIGS. 1–5, the container part 1 has an elongate form with a front surface 9, a rear surface 10 opposite to the front surface 9, two side surfaces 11 opposite to each other and an end surface 12. The afore-mentioned opening 7 on the container part is situated at a distance from the end surface 10 and the periphery of the opening 7 is delimited by the front, rear and side surfaces of the container part. The rear surface 10 preferably has an extension in the longitudinal direction 3 that is greater than that of the front surface 9, and as a result the side surfaces 11 are slanted at the opening 7. The end surface 12 preferably has a rounded form without sharp corners so that the package will have a small and compact form that does not catch or stick on various objects when the package is stored in, for example, a handbag. The other surfaces of the container part are also arranged by each other with gradual transitions without sharp corners or edges, see the figures.

Figure 3:
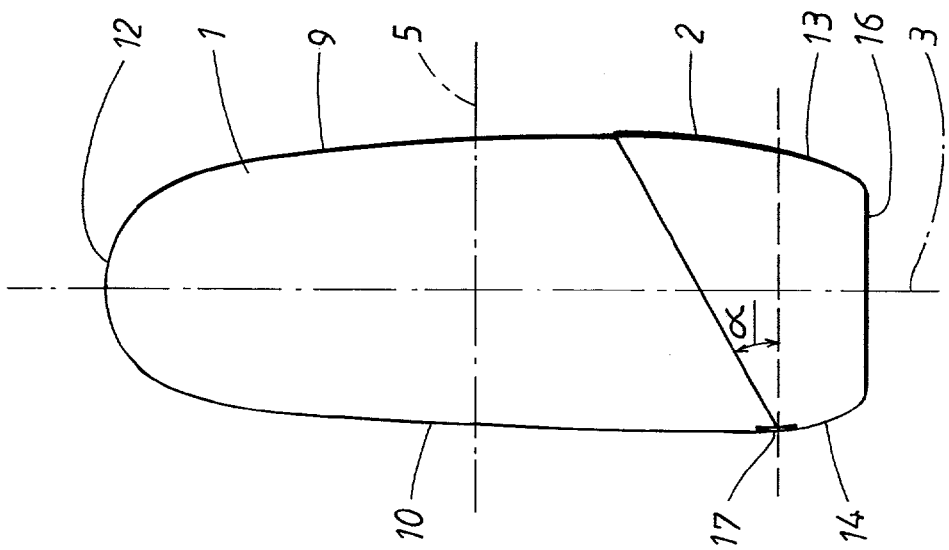
FIG. 3 shows a closed package in accordance with the invention seen from the side.

Similar to the container part 1, the lid part 2 has a front surface 13, a rear surface 14 opposite to the front surface 13, two side surfaces 15 opposite to each other and an end surface 16. The opening 8 on the lid part is situated at a distance from the end surface 16 and the periphery of the opening 8 is delimited by the front 13, rear 14 and side 15 surfaces of the lid part. On the lid part the rear surface preferably has an extension in the longitudinal direction 3 that is less than that of the front surface 13, with the result that the side surfaces 15 are also slanted in order to be adapted to the container part 1. The end surface 16 on the lid part is preferably flat so that, during transport and sale the package can stand upright with the lid part arranged downwards and the container part upwards, as shown in FIGS. 3 and 4. Also on the lid part the different surfaces are arranged by each other with gradual transitions without sharp corners or edges.

The opening 7 in the container part and the opening 8 in the lid part are designed so that the lid part 2 can cooperate releasably with the container part 1, i.e. the package is opened by removing the lid part from or displacing it in relation to the container part. In accordance with a preferred embodiment, the lid part 2 is connected to the container part by means of a joint member 17, for example a hinge, which is placed so that the rear surface 10 of the container part is connected to the rear surface 14 of the lid part. In this way, the lid part is pivotably joined in relation to the container part by means of the joint member and the package can then be opened by pushing the front surface 13 of the lid part away from the container part, see FIG. 1.

The slanted design of the side surfaces 11, 15 of the container and lid parts and the situation of the joint member 17 on the rear surface 10 of the container part high up on the package means that it is possible to make the package small and compact without the risk of the front surface 13 of the lid part catching in the stack 100 when the package is opened. Due to the fact that the front surface 9 of the container part has a longitudinal extension 3 that is smaller than that of the rear surface 10, it is also easy to access the panty liners in the container after the lid part has been swung up in relation to the container part. The angle on the periphery of the side surfaces 11, 15 at the openings on the container and lid parts in relation to the height direction can be varied depending on the design of the package. Suitably, the angle α, which has its apex in the joint member 17 and runs from a line that is parallel with the height direction to the periphery of the side surfaces 11, 15 at the openings when the package is closed, is within the interval 0°–70°, see FIG. 3. According to a preferred embodiment, the angle α is approximately 30°. It is also possible within the scope of the invention to make the opening such that the angle α is negative.

Due to the rounded form of the end surface 12 of the container part, the upper surface of the stack 100 is given a somewhat concave form when it is stored in the package (see FIG. 1), as those panty shields that lie in the middle of the stack end up further down in the package than those that lie at the outer edges of the stack. The concave form of the stack makes it easier for the user to take hold of the panty shield lying foremost in the stack nearest the front surface 9 of the container part and in this way the user can avoid more than one panty shield being taken out of the package at a time. The end surface 12 need not be rounded but can, alternatively, be undulating or have some other irregular form in order to give the upper surface of the stack a form that facilitates removal of panty shields. The end surface 12 can also be flat so that the package can stand upright with the container part arranged downwards during transport and sale. In a corresponding manner, the end surface 16 of the lid part need not be flat but can, alternatively, have a rounded or irregular form.

Figure 6:
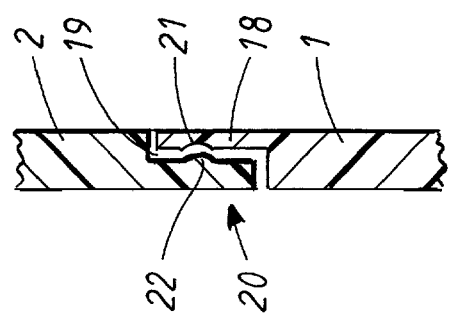
FIG. 6 shows a cross section along the line VI—VI through the closed package in FIG. 4.
Figure 5:
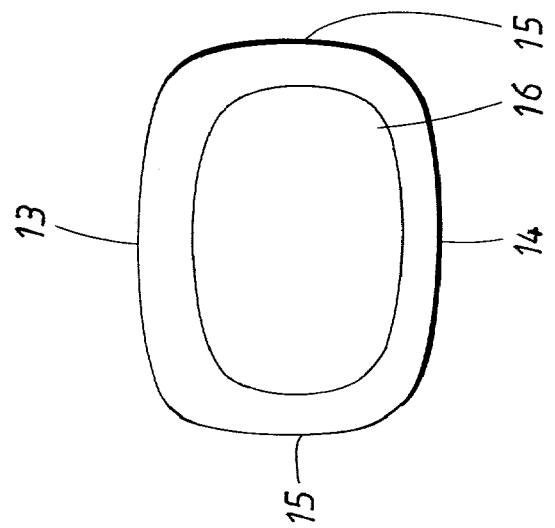
FIG. 5 shows an end view of the closed package.

In order to prevent dirt, dust or the like from penetrating into the package, a rim 18 is arranged on the container part 1, suitably along the entire periphery on the opening 7 of the container part. In a corresponding manner, the area along the periphery of the opening 8 of the lid part is provided with a recess 19, which can cooperate with the rim 18 when the package is closed by pivoting the lid part towards the container part. The rim 18 is adapted to the recess 19 and in the closed position the rim 18 thus ends up in the recess 19, as a result of which the rim 18 gives a tight seal and functions as a barrier against dirt, dust or the like (see FIG. 6). Alternatively, it is possible within the scope of the invention to arrange the rim on the lid part and the recess on the container part. A suitable way to construct the rim and the recess is simply to let the lid and container parts have a lesser material thickness at their respective openings (see FIG. 6).

An important characteristic for the package is that it is shockproof. It should preferably therefore be manufactured from a material that does not break when the package is subjected to pressure, blows or knocks during normal use, or if the package should be dropped on the floor or the ground. Furthermore, when the package is closed it should be formed in such a way that the lid part sits securely on the container part so that the package does not open of its own accord when it is being stored, for example in a handbag, or is subjected to blows or knocks. Thus, it is expedient that the lid part is constructed and designed in such a way in relation to the container part that a certain force is required to open the package. The force should be sufficiently great to ensure hygienic storage but at the same time the package must not be perceived as being difficult to open. It is possible to ensure safe storage of the panty shields by arranging a locking mechanism in the form of a snap lock 20 on the package. The snap lock 20 is suitably arranged in connection with the rim 18 and the recess 19. In the embodiment according to FIGS. 1–6, the rim 18 along a part of its periphery, preferably on the front surface 9 of the container part, is provided with a tab 21 and the recess 19 along a part of its periphery, preferably on the front surface 13 of the lid part, is provided with a notch 22 which conforms to the tab 21. Due to the fact that the container part and the lid part are somewhat flexible, the tab can take hold of the notch when the package is closed, with the result that the lid part is locked tightly to the container part. The package is opened by pushing the lid part away from the container part at the snap lock 20 with a force which exceeds the holding power of the snap lock. In order to facilitate opening, it is also possible to press the front surface of the container part down immediately under the snap lock in order to free the tab 21 from the notch 22 while at the same time pushing the lid up. To facilitate the pressing down, the front surface of the container part can be provided with a thumb grip 23 in the form of a dip in the surface (see the figures). By varying the form of the tab 21 and the notch 22 in the longitudinal and transverse directions and also along the periphery of the openings 7, 8 of the lid and container parts, the holding power of the snap lock 20 can be varied. It is also possible in the present invention to arrange the tab 21 and the notch 22 on the lid part and the container part, respectively, or to use other types of snap lock or holding devices such as hooks or the like.

If the package is to offer hygienic storage of the absorbent articles, it is important that it protects the articles from blows or knocks and at the same time efficiently prevents dirt and dust from penetrating in and spoiling the articles. The package can be made shape stable by giving it a form that is adapted to its purpose and by manufacturing it from a suitable material. The term shape stable is intended to mean that the package does not become deformed to any appreciable degree by any strain it can be subjected to during normal use, for example when it is carried around in a handbag or the like. That the package is shape stable also implies that it shall tolerate knocks and blows without appreciable deformation and shall regain or essentially regain its original form if it is deformed.

Suitable materials for the package are transparent, semi-transparent or opaque plastics, such as for example polystyrene (PS), polyvinyl chloride (PVC), polyethylene (PE), polypropylene (PP) or polyethylene terephthalate (PET), and polypropylene (PP) is preferably used. By using a transparent or semi-transparent material during manufacture, the package can be formed so that it is possible to see the stack of panty shields from the outside. The package can be manufactured by injection moulding, blow moulding or vacuum moulding. In injection moulding, a mould provided with a cavity which corresponds to the dimensions of the package is used. During the actual injection moulding, a molten plastic is pressed into the cavity and after the plastic has set, the package is taken out of the mould. Preferably, the whole package is injection moulded with both the lid and container parts and also the joint member of the same material in a single continuous unit. The material thickness of the package should lie within the range of 0.5–3.5 mm and is suitably 1.2 mm and the package preferably has the same material thickness over essentially its entire extension. During manufacture, it is possible to provide the surfaces of the package with different surface structures or design elements such as graphic designs, logos or the like in order to give it an attractive and pleasant appearance. The design elements can expediently be formed directly during the injection moulding by engraving the actual mould with relief patterns which are reproduced on the package or by the tool having alternating matte and shiny surfaces which give patterns in matte and shiny surfaces on the package. It is also possible to provide the package with patterns or the like after it has been taken out of the mould. As the package is suitably made of plastic, it is possible to give it different colors to make it look attractive.

A suitable number of absorbent articles for the package can lie, for example, within the range of 2–40, depending on which type of absorbent article is to be packed and on how great an extension in the height direction the package is to have. The extension of the package in the height direction can easily be adapted to a suitable number of articles. The extension of the package in the longitudinal and transverse directions is completely dependent on the extension of the absorbent articles in the corresponding directions and the size and form of the storage space will here form the basis of the extension of the package. A package for small absorbent articles such as micro panty shields or the like should, in the closed position, have a greatest length in the longitudinal direction of about 70–150 mm, a greatest width in the transverse direction of about 40–70 mm and a greatest height in the height direction within the range of about 5–60 mm depending on the height of the stack. In accordance with one particular preferred embodiment, the package has a greatest length of about 100 mm, a greatest width of about 50 mm and a greatest height of about 39 mm.

Figure 7:
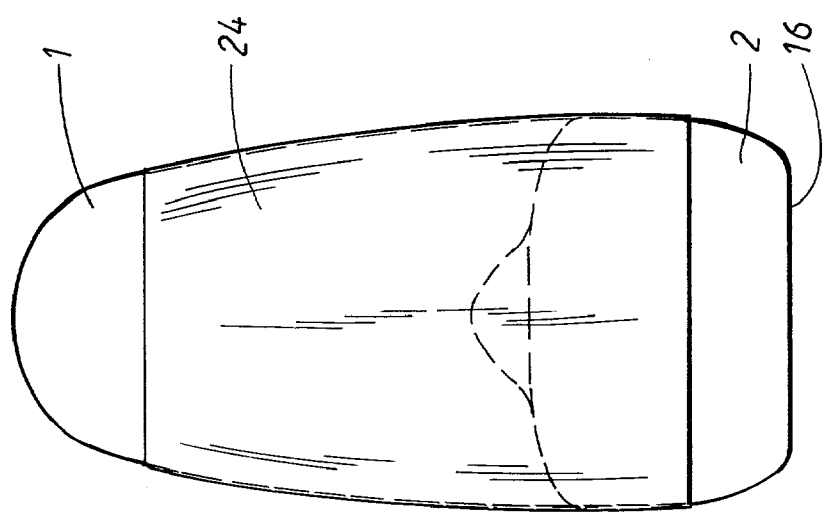
FIG. 7 shows a closed package provided with a girdle.

After the stack 100 of panty shields 101 has been packed in the package and the lid part has been closed properly, it is suitable to provide the package with an extra protection to ensure for a customer that it is unopened when it is offered for sale. An effective way to prevent undesired opening of the package before sale is to provide it with a girdle or circumferential band 24 made of a plastic film or the like, which encircles at least a part of the container part 1 and also a part of the lid part 2 in the area on the outside of the package where the opening 7 of the container part cooperates with the opening 8 of the lid part (see FIG. 7). Due to the band 24 being placed over both the container and lid parts and it being constructed in such a way that it must be removed before opening of the package, it is easy for the customer to see if the package has been opened or not. The band can be manufactured of a shrink film of, for example, polyethylene terephthalat (PET) or, more preferably, orientated polystyrene (OPS), which is formed as a tube that is slipped over the package and then warmed up carefully so that it closes round the package. In order to facilitate the removal of the band, it is possible to provide it with a perforation, tear arrangement, or the like. It is also suitable to provide the band with product information, trademarks, or the like since it is much simpler and cheaper to print this type of information on a plastic film than on the actual container. In order to be able to provide the package with as much information as possible, the band should be formed so that it covers the greater part of the surface of the package. As it is possible to print on the band, it can advantageously be used to strengthen the visual impression of the package when it is on sale and at the same time the package can be made discreet when the band is removed.

Within the scope of the invention, it is possible to place the opening of the package in another way than that described above, in which the package is divided in the longitudinal direction 3 into a container part and a lid part 2. For example, it is possible to form the package so that it is divided in the transverse or height direction. It is also possible to form the opening in another way and to form the container and lid parts with straight side surfaces.

A suitable absorbent article for this type of package is panty shields or sanitary napkins. A so-called micro panty shield suitable for the package will be described in further detail below. A micro panty shield is distinguished by the fact that it has a small extension in the longitudinal and transverse directions compared with a traditional panty shield. The panty shield has a length in the longitudinal direction which lies within the range of about 65–100 mm and a greatest width in the transverse direction within the range of about 35–55 mm. According to a particular preferred embodiment, the panty shield has a length of about 91 mm and a greatest width of about 42 mm.

Figure 8:
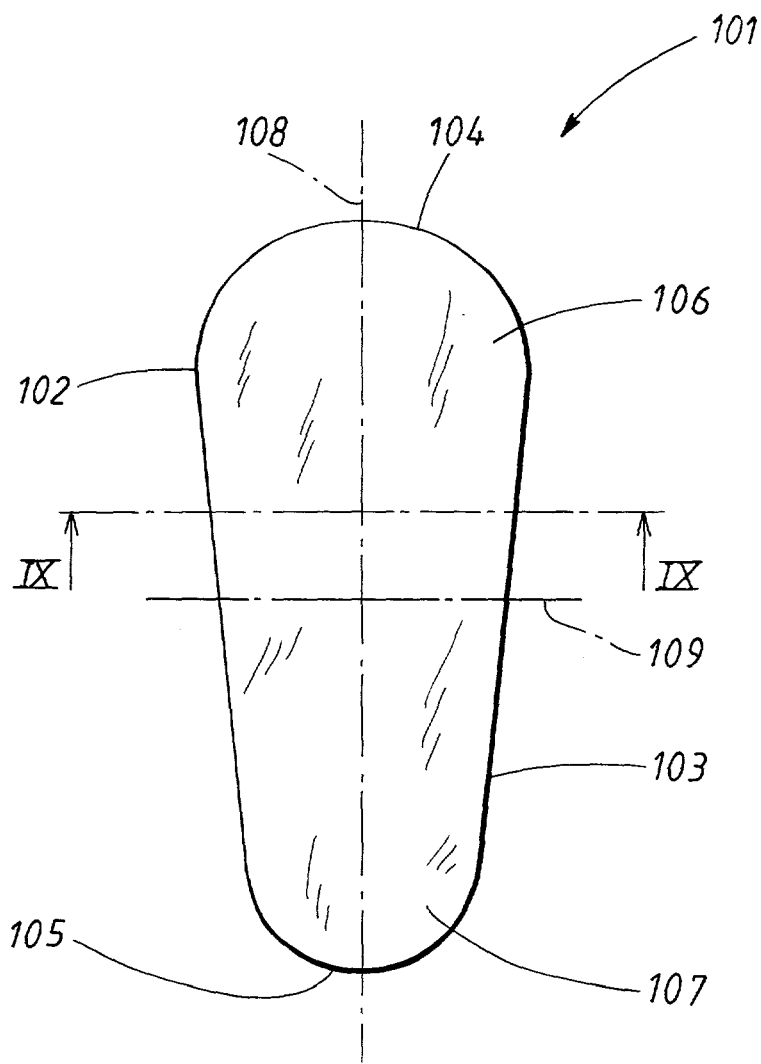
FIG. 8 shows a micro panty shield seen from above.
Figure 9:
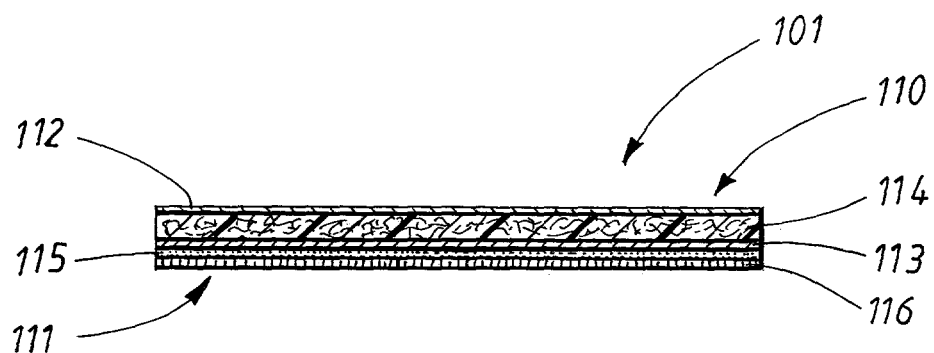
FIG. 9 shows a section along the line IX—IX through the panty shield in FIG. 8.

The panty shield 101 in FIGS. 8 and 9 has an essentially elongate form with a longitudinal direction 108 and a transverse direction 109 and displays two long sides 102, 103, two short sides 104, 105, a first end portion 106 intended to face forwards on the user, a second end portion 107 intended to face rearwards on the user. The panty shield has an upper side 110, which is intended to face towards the user during use, and an underside 111, which is intended to face away from the user during use.

The panty shield comprises a liquid-permeable surface layer 112 arranged on the upper side so that it is facing towards the user during use and a liquid-impermeable rear-side layer 113 on the underside. Between the surface layer 112 and the rear-side layer 113 an absorbent body 114 is arranged. The surface layer and the rear-side layer are suitably connected to the absorbent body with glue. The surface layer 112 and the rear-side layer 113 can have the same extension in the longitudinal and transverse directions as the absorbent body 114 (see FIG. 9). It is also possible to form the panty shield so that the surface layer 112 and the rear-side layer 113 have a greater extension than the absorbent body 114. In that case, the surface layer and the rear-side layer are connected to one another in the area outside the absorbent body around the periphery of the absorbent body, wherein a hem is formed around the edge of the panty shield. During manufacture of the panty shield, the different layers can be pressed together during gluing with an embossed roll, for example around the edge of the panty shield. It is also possible to emboss a pattern into the article during manufacture.

FIG. 9 shows a section through the panty shield in FIG. 8 along the line IX—IX. Fastening members in the form of pressure-sensitive glue 115 are arranged on the underside of the panty shield. The glue 115 can cover the entire underside, be applied in parallel strips along the underside or be applied on the underside in another suitable pattern, such as check patterns or spots. A removable protective layer 116 is arranged over the glue 115 and the protective layer 116 is removed by the user before application of the panty shield in the user's undergarments. The protective layer 116 may be, for example, a so-called release paper, which can be constituted by a paper layer coated with silicon.

The surface material 112 may be any conventional material, for example nonwoven, perforated plastic film or a laminate of a perforated plastic film and a nonwoven.

The rear-side layer 113 may be a liquid-impermeable material, such as a thin liquid-tight plastic film, or a material which in itself is liquid-permeable and which has then been coated with a layer of plastic, resin or some other liquid-tight material. The barrier layer 113 can thus include any material that fulfills the criterion of liquid-impermeability so that leakage from the underside is prevented and displays sufficient flexibility and skin-friendliness for the purpose. Examples of suitable materials are plastic films of polyethylene, polyester or polypropylene, nonwoven and laminates of nonwoven and plastic films. A rear-side layer which includes a laminate of a liquid-impermeable plastic layer, turned towards the absorbent layer, and a nonwoven turned towards the undergarments of the user gives a leakage-safe barrier layer with a textile feel. It is also possible to form the rear side of the panty shield with a breathable rear-side layer of, for example, SMS (spunbond-meltblown-spunbond) or of a breathable plastic film of, for example, polyethylene.

The absorbent body 114 is suitably produced from natural fibers, such as cellulose fluff, absorbent synthetic fibers or mixtures of natural fibers and synthetic fibers. Preferably, the absorbent body 114 includes a so-called airlaid, i.e. an airlaid cellulose body. It is also possible to mix in so-called superabsorbents in the absorbent body. A superabsorbent is a polymer with an ability to absorb several times its own weight of liquid. The absorbent body 114 can also contain further components as shape-stabilizing members, liquid-dispersion members or binding means. It is also possible to use different kinds of absorbent foam material in the absorbent body.

An admission layer may be arranged between the surface layer and the absorbent body. The admission layer has the task of drawing in liquid into the absorbent article and transporting the liquid down to the absorbent body 114. The admission layer can be made of, for example a nonwoven material with low density.

The panty shield 101 can have another form than that described above. Other conceivable forms of this type of absorbent article can be, for example, rectangular, triangular, hour-glass-shaped, round or oval. The package can then have another form than that which has been described, as its design is decided by the form of the absorbent body.

The invention should not be considered to be limited to the above embodiments as these are merely intended to clarify the invention. Within the scope of the invention it is also possible to combine characteristics from different embodiments with each other.

What is claimed is:

1. A package system, the package system comprising:
   a plurality of non-folded, thin absorbent articles placed adjacent each other in a stack, said plurality of absorbent articles each having a first end portion and a second portion defining an absorbent article length therebetween, said plurality of absorbent articles having similar lengths;
   a package for hygienic storage of the stack of absorbent articles, said package including a container part and a lid part, the container part having an end surface and an upper rim surface;
   wherein the container part and the lid part together cooperate to delimit a storage space intended to accommodate the stack, such that the storage space has a form that principally conforms to the form of the stack;
   wherein said container part is adapted to receive the first end portions of the absorbent articles in the stack proximal the bottom end of said container part such that the second end portions of the absorbent articles extend above the upper rim surface of said container part;
   wherein said lid part includes a recess adapted to receive the second end portions of the absorbent articles in the stack, when said package is in a closed position;
   wherein said container part has a greatest width defined in a transverse direction; said length of said absorbent article being greater than said greatest width of said container part;
   wherein the end surface of said container part has a rounded form and the first end portions of the absorbent articles proximal thereto are correspondingly displaced relative to the rounded form such that the second end portions of the absorbent articles extending above the upper rim surface of said container part exhibit a concave form, thereby enabling a user to more easily grasp a foremost one of said absorbent articles; and
   wherein said package is shape stable and shock-proof.

2. A package in accordance with claim 1, wherein the container part has an opening which cooperates with an opening arranged on the lid part so that a tight seal is obtained between the openings, and wherein the container part is provided with a rim which is adapted to a recess in the lid part.

3. A package in accordance with claim 1, wherein the container part is provided with a front surface, a rear surface opposite to the front surface, and two opposing side surfaces, and the lid part is provided with a front surface, a rear surface opposite to the front surface, two opposing side surfaces and an end surface.

4. A package in accordance with claim 1, wherein the absorbent articles include micro panty shields.

5. A package in accordance with claim 3, wherein the end surface of the lid part is flat.

6. A package in accordance with claim 3, wherein the lid part is pivotably attached to the container part by means of a joint member.

7. A package in accordance with claim 6, wherein the joint member connects the rear surface of the container part with the rear surface of the lid part.

8. A package in accordance with claim 3, further comprising a locking mechanism in the form of a snap lock.

9. A package in accordance with claim 8, wherein the container part is provided with a rim which is adapted to a recess in the lid part, and the snap lock is arranged adjacent to the rim and the recess, wherein the rim along a part of its periphery is provided with a tab and the recess along a part of its periphery is provided with a notch such that the tab can take hold of the notch when the package is closed and the lid part can be locked to the container part.

10. A package in accordance with claim 1, wherein said package is manufactured from a plastic material.

11. A package in accordance with claim 1, wherein in a closed position said package has a greatest length in a longitudinal direction of about 70–150 mm, and a greatest width in a width direction of about 40–70 mm, and a greatest height in a height direction within an interval about 5–60 mm.

12. A package in accordance with claim 1, further comprising a band encircling at least a part of the container part as well as a part of the lid part in the area on the outside of the package where the opening of the container part cooperates with the opening of the lid part.

13. A package in accordance with claim 12, wherein the band is manufactured from a shrink film of orientated polystyrene (OPS).

14. A package in accordance with claim 12, wherein the band is provided with a perforation or tear arrangement.

15. A package in accordance with claim 9, wherein said tab is provided on the front surface of the container part and said notch is provided on the front surface of the lid part.

16. A package in accordance with claim 10, wherein the plastic material comprises polypropylene.

17. A package in accordance with claim 11, wherein said package has the greatest length in the longitudinal direction of about 100 mm, and the greatest width in the width direction of about 50 mm, and the greatest height in the height direction of about 39 mm.

18. A package in accordance with claim 12, wherein said band comprises a plastic film.

* * * * *